United States Patent
Aubert et al.

(10) Patent No.: US 11,154,464 B2
(45) Date of Patent: Oct. 26, 2021

(54) AEROSOL DEVICE FOR HAIR SHAPING AND/OR HAIRSTYLE HOLD

(71) Applicant: L'OREAL, Paris (FR)

(72) Inventors: Lionel Aubert, Saint-Ouen (FR); Céférino Rodrigues, Saint-Ouen (FR); Catherine Tetu, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/491,375

(22) PCT Filed: Mar. 9, 2018

(86) PCT No.: PCT/EP2018/055904
§ 371 (c)(1),
(2) Date: Sep. 5, 2019

(87) PCT Pub. No.: WO2018/162711
PCT Pub. Date: Sep. 13, 2018

(65) Prior Publication Data
US 2020/0016046 A1    Jan. 16, 2020

(30) Foreign Application Priority Data
Mar. 9, 2017 (FR) ...................................... 1751946

(51) Int. Cl.
*A61K 8/02* (2006.01)
*A61K 8/04* (2006.01)
(Continued)

(52) U.S. Cl.
CPC ............ *A61K 8/0241* (2013.01); *A61K 8/046* (2013.01); *B05B 1/14* (2013.01); *B65D 83/28* (2013.01);
(Continued)

(58) Field of Classification Search
CPC ........ A61K 8/0241; A61K 8/046; A61K 8/19; A61K 2800/31; A61K 2800/412;
(Continued)

(56) References Cited

U.S. PATENT DOCUMENTS

| | | |
|---|---|---|
| 4,557,916 A | 12/1985 | Withiam |
| 5,690,924 A | 11/1997 | Keil et al. |

(Continued)

FOREIGN PATENT DOCUMENTS

| | | |
|---|---|---|
| EP | 0452208 A1 | 10/1991 |
| EP | 2444160 A1 | 4/2012 |

(Continued)

OTHER PUBLICATIONS

International Search Report and Written Opinion for counterpart Application No. PCT/EP2018/055882, dated May 4, 2018.
(Continued)

*Primary Examiner* — Jeffrey T. Palenik
(74) *Attorney, Agent, or Firm* — The Marbury Law Group, PLLC

(57) ABSTRACT

The present invention relates to an aerosol device comprising: —a container containing a cosmetic composition which comprises one or more powders in a content of less than 7% by weight relative to the total weight of the composition, and—a dispensing head comprising a body and an end part comprising at least two outlet orifices configured to allow spraying of the composition about a longitudinal axis of the end part in at least two different directions, the dispensing head comprising at least first and second chambers, through which the composition stream successively passes before it exits via the outlet orifices.

20 Claims, 7 Drawing Sheets

Figure 1:
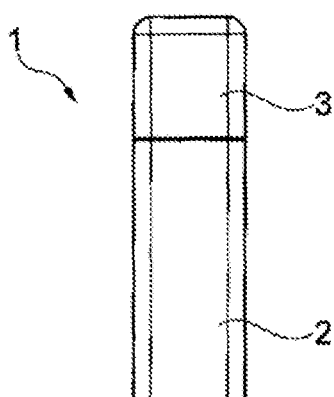

(51) Int. Cl.
  *B05B 1/14* (2006.01)
  *B65D 83/28* (2006.01)
  *B65D 83/14* (2006.01)
  *A61K 8/19* (2006.01)
  *A61K 8/73* (2006.01)
  *A61K 8/81* (2006.01)
  *A61K 8/88* (2006.01)
  *A45D 34/00* (2006.01)
  *A61K 8/25* (2006.01)
  *A61K 8/26* (2006.01)
  *A61Q 5/06* (2006.01)

(52) U.S. Cl.
  CPC .............. *B65D 83/752* (2013.01); *A61K 8/19* (2013.01); *A61K 8/732* (2013.01); *A61K 8/8147* (2013.01); *A61K 8/88* (2013.01); *A61K 2800/412* (2013.01); *A61K 2800/87* (2013.01)

(58) Field of Classification Search
  CPC ...... A61K 2800/87; A61K 8/022; A61K 8/25; A61K 8/26; A61K 8/732; A61K 8/8147; A61K 8/88; A45D 34/00; A61Q 5/06; B05B 1/14; B65D 83/28; B65D 83/752; Y02T 10/62
  See application file for complete search history.

(56) References Cited

U.S. PATENT DOCUMENTS

| | | |
|---|---|---|
| 2002/0017575 A1 | 2/2002 | Andrews et al. |
| 2003/0150937 A1 | 8/2003 | Laidler et al. |
| 2009/0218418 A1 | 9/2009 | Sharief |
| 2015/0104397 A1 | 4/2015 | Small et al. |
| 2015/0139917 A1 | 5/2015 | Gawtrey et al. |
| 2016/0075501 A1 | 3/2016 | Aubert et al. |
| 2016/0100667 A1 | 4/2016 | Aubert et al. |
| 2018/0016087 A1 | 1/2018 | Smail et al. |
| 2018/0243763 A1* | 8/2018 | Eurippini ............... B65D 83/28 |

FOREIGN PATENT DOCUMENTS

| | | | |
|---|---|---|---|
| FR | 2990131 A1 | 11/2013 | |
| FR | 2990133 A1 | 11/2013 | |
| FR | 3004901 A1 | 10/2014 | |
| FR | 3004902 A1 | 10/2014 | |
| FR | 3004929 A1 | 10/2014 | |
| FR | 3031437 A1 | 7/2016 | |
| FR | WO 2016/110575 * | 7/2016 | ............... A61Q 5/06 |
| GB | 2340891 A | 3/2000 | |
| JP | 2003-326197 A | 11/2003 | |
| WO | 03/045573 A1 | 6/2003 | |
| WO | 2011/056625 A1 | 5/2011 | |
| WO | 2014/177646 A2 | 11/2014 | |
| WO | 2014/177647 A1 | 11/2014 | |
| WO | 2016/092109 A1 | 6/2016 | |
| WO | 2016/110575 A1 | 7/2016 | |
| WO | 2016/110578 A1 | 7/2016 | |
| WO | 2018/162701 A1 | 9/2018 | |
| WO | 2018/162707 A1 | 9/2018 | |

OTHER PUBLICATIONS

International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Brunauer et al., "Adsorption of Gases in Multimolecular Layers," Journal of the American Chemical Society, vol. 60, Feb. 1938, pp. 309-319.
Non-Final Office Action for copending U.S. Appl. No. 16/491,372, dated May 28, 2020.
NPL Search String: IQQueryQuickExport 202005221756, downloaded May 22, 2020.
NPL Search String: IQQueryQuickExport 202005221759, downloaded May 22, 2020.
Non-Final Office Action for copending U.S. Appl. No. 16/491,374, dated Jan. 14, 2021.
Final Office Action for copending U.S. Appl. No. 16/491,372, dated Dec. 18, 2020.

* cited by examiner

AEROSOL DEVICE FOR HAIR SHAPING AND/OR HAIRSTYLE HOLD

CROSS REFERENCE TO RELATED APPLICATIONS

This is a national stage application of PCT/EP2018/055904, filed internationally on Mar. 9, 2018, which claims priority to French Application No. 1751946, filed on Mar. 9, 2017, both of which are incorporated by reference herein in their entireties.

The present invention relates to an aerosol device comprising a particular dispensing means and a composition based on at least one powder, and to a process for treating the hair, especially for shaping the hair and/or holding the hairstyle.

The hair products for shaping and/or holding the hairstyle that are the most widespread on the cosmetics market are spray compositions, such as lacquers and sprays or compositions dispensed in the form of foams. They essentially consist of an alcoholic or aqueous solution and of one or more materials, generally polymeric resins, also referred to as fixing polymers, whose function is to form welds between the individual hairs or to coat the hairs, as a mixture with various cosmetic adjuvants.

These products provide fixing and hold of the hairstyle over time. In practice, however, these products are not entirely satisfactory, especially in terms of the cosmetic qualities on the hair. The aerosol sprays conventionally used which generate a spray or a foam, when applied to all or part of the hair, are liable to create fibre irregularities along an individual hair on account of the diffusion of the spray in the form of droplets or by spreading of the foam.

Aerosol devices comprising three outlet orifices have already been proposed for dispensing shaping products, especially in patent application EP 2 991 735, the three orifices spraying the composition in the same direction.

Patent application US 2002/0017575 describes a spray device comprising one or more spray stems pierced with orifices allowing a product to be diffused in the hair.

There is thus a need to develop a new aerosol device comprising a hair shaping composition which can afford good shaping of the hairstyle while at the same time obtaining a good level of cosmeticity.

The Applicant has found, surprisingly and advantageously, that the use of a device equipped with a dispensing head comprising at least two outlet orifices for spraying the composition in at least two different directions and at least two chambers through which the composition stream successively passes before it exits via the outlet orifices to dispense a composition comprising at least one powder in a particular content allows a hairstyle to be shaped easily and quickly, with satisfactory and long-lasting volume.

The changes of direction of the composition stream in the dispensing head create turbulences in the composition stream, which produces good-quality sprays.

According to a first of its aspects, a subject of the invention is an aerosol device comprising:

a container containing a cosmetic composition which comprises at least one powder in a content of less than 7% by weight relative to the total weight of the composition, and a dispensing head comprising a body and an end part comprising at least two outlet orifices configured to allow spraying of the composition about a longitudinal axis of the end part in at least two different directions, the dispensing head comprising at least first and second concentric chambers through which the composition stream successively passes before it exits via the outlet orifices, the dispensing head comprising at least one aperture between the first and second concentric chambers which is angularly offset relative to at least one of the outlet orifices.

This particular combination makes it possible mainly to apply the product at the root, thus improving the cosmetic qualities of the hair after application by maintaining a natural non-rigid effect while at the same time obtaining satisfactory volume.

The present invention also relates to a process for treating the hair, and in particular for shaping the hair and/or holding the hairstyle, which comprises the use of the device as defined above. In particular, the hair treatment process comprises a step of applying, to dry or wet hair, a composition sprayed from an aerosol device according to the invention, optionally to be rinsed off after an optional leave-on time or after optional drying.

Other subjects, characteristics, aspects and advantages of the invention will emerge even more clearly on reading the description and the example that follows.

In the text hereinbelow, and unless otherwise indicated, the limits of a range of values are included within that range, especially in the expressions "between" and "ranging from . . . to . . . ".

Moreover, the expression "at least one" used in the present description is equivalent to the expression "one or more".

According to the invention, the aerosol device comprises a container which contains a cosmetic composition comprising one or more powders.

The powder may be mineral or organic, preferably mineral. It may especially be a filler, a pigment or a mixture thereof.

For the purposes of the present invention, the term "filler" means natural or synthetic particles of any form, which are insoluble in the medium of the composition, irrespective of the temperature at which the composition is manufactured.

The fillers may be organic or inorganic, and may be of any form such as lamellar, spherical or oblong, irrespective of the crystallographic form (for example cubic, hexagonal, orthorhombic, rhombohedric or tetragonal). In a preferred embodiment, the fillers are not spherical.

For the purposes of the present invention, the term "pigment" means organic or mineral, white or coloured particles of any form, which are insoluble in the medium containing them and which give the composition a colour.

The term "mineral" encompasses natural or synthetic chemical compounds that are inorganic. Mineral substances are mainly in a crystalline form.

Examples of mineral or inorganic powders that may especially be mentioned include:

fillers such as metal carbonates, oxides and sulfates such as those of alkaline-earth metals, aluminium, gallium and indium; silicates; modified or unmodified silicas; sericite, synthetic fluorophlogopite, talc; natural or synthetic mica, especially white mica, gold mica, red mica, black mica and mica-lithium oxide; calcium phosphate, silicic acid, silicic anhydride, silicon carbide, metal salts of tungstic acid, magnesium aluminate, bentonite, zeolites, smectite, hydroxyapatite, ceramic powder, boron nitride and glass or ceramic microcapsules;

specific composite fillers such as those sold under the names Excel Mica, Excel Pearl and the powder La Vie by the company Miyoshi Kasei, Inc.;

white pigments such as titanium dioxide, zinc oxide, zirconium oxide and cerium oxide;

coloured pigments such as red iron oxide, yellow iron oxide, black iron oxide, chromium oxide, chromium hydroxide, Prussian blue, ultramarine blue, chromium hydrate, ferric blue, inorganic blue pigments, carbon black, lower titanium oxides, manganese violet, cobalt violet, and metal powders such as aluminium powder and copper powder;

nacreous pigments such as bismuth oxychloride, mica/titanium, essence of pearl, powder prepared by coating synthetic mica with titanium dioxide, powder prepared by coating silica flakes with titanium dioxide, which is available under the brand name Metashine from Nippon Sheet Glass Co., Ltd, powder prepared by coating alumina flakes with tin oxide and titanium dioxide, powder prepared by coating aluminium flakes with titanium dioxide, powder prepared by coating copper flakes with silica, sold by the company Eckert Inc. USA, powder prepared by coating bronze flakes with silica, and powder prepared by coating aluminium flakes with silica;

ultrafine powders, having a mean particle size of less than 0.1 μm, such as ultrafine titanium dioxide, ultrafine zinc oxide, ultrafine iron oxide, and ultrafine cerium oxide;

other powders such as the luminescent powder sold under the brand name Luminova Series by Mitsui & Co., Ltd., aluminium powder, stainless-steel powder, tourmaline powder, and amber powder; and a mixture thereof.

Examples of organic powders are starch powder or starch derivative powder, cork powder, quinoa powder, wool powder, polyamide powder (Nylon® or Orgasol® from Arkema), polyester powder, polyethylene powder, polypropylene powder, polystyrene powder, polyurethane powder, benzoguanamine powder, polymethyl benzoguanamine powder, tetrafluoroethylene powder, poly(methyl methacrylate) powder, cellulose powder, silk powder, silicone powder, silicone rubber powder, powders of synthetic resins such as a styrene/acrylate copolymer, a divinylbenzene/styrene copolymer, a vinyl resin, a urea resin, a phenolic resin, a fluoro resin, tetrafluoroethylene (Teflon®) polymers, a silicone resin, an acrylic resin, a melamine resin, an epoxy resin, and a polycarbonate resin, hollow polymer microspheres, such as those of poly(vinylidene chloride)/acrylonitrile, for example Expancel® (Nobel Industrie), or acrylic acid copolymers (Polytrap® from the company Dow Corning), silicone resin microbeads (for example Tospearls® from Toshiba), particles formed from polyorganosiloxane elastomers, microcrystalline fibre powder, starch powder, acylated lysine powder, poly-β-alanine, lauryllysine, powder of the metal salt of (long-chain alkyl) phosphate, metal soap powder, Colour Index (CI) yellow pigments, CI orange pigments and tar-based pigments prepared in lacquer form, and dyes existing in the natural state prepared in lacquer form.

The tar-based dyes include, for example, the dyes Red No. 3, Red No. 10, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

The natural dyes include powders such as carmine, laccaic acid, carsamine, brazilin and crocin.

The doped or undoped composite powder may also be suitable as base powder intended to undergo a surface treatment. Examples of the latter include the powder prepared by coating inorganic dye pigments such as red iron oxide with silicic anhydride, powders prepared by coating Nylon with white pigments and powders prepared by coating fillers with ultrafine white pigments.

The mineral powder(s) according to the invention may optionally be surface-modified with organic compounds.

Preferably, the powder is a mineral powder constituted of one or more water-insoluble mineral compounds.

For the purposes of the present invention, the term "water-insoluble" refers to a compound whose solubility at spontaneous pH in water at 25° C. and at atmospheric pressure is less than 0.1%.

The water-insoluble mineral compound(s) are preferably chosen from metal carbonates, oxides and sulfates, silicates, modified or unmodified silicas, mica, talc, and mixtures thereof.

Examples that may more particularly be mentioned include the carbonates, oxides and sulfates of alkaline-earth metals such as beryllium, magnesium, calcium, strontium, barium and radium, better still magnesium and calcium; the oxides, sulfates and carbonates of aluminium, gallium and indium; silicates such as kaolinite or kaolins (natural silicates containing kaolinite), silicates containing magnesium, particularly those containing an amount of magnesium of greater than 10% by weight (on a dry basis) expressed as magnesium oxide, such as Li—Mg—Na silicates, for instance Laponite XLG, proposed by the company Rockwood; modified or unmodified silicas, better still modified silicas; mica; talc; and mixtures thereof.

Among the modified silicas, it is preferred to use surface-treated silicas such as hydrophobic silicas, for instance hydrophobic fumed silica of nanometric size and surface-treated with hexamethyldisilazane, such as the silica sold under the trade name Aerosil R812S or Aerosil R972 by the company Evonik, or HDK H115 by the company Wacker, or the hydrophobic fumed silica surface-treated with dimethylsilane.

The powder may be a styling powder, i.e. it has a capacity for shaping the head of hair or for the durability of this shaping.

The capacity for shaping or shaping durability of the powder may especially be due to its chemical nature and/or its geometrical form and/or its arrangement configuration during deposition onto the keratin fibre. Specifically, the irregularities created at the surface of the hair promote the inter-attachment of the fibres.

The powder may be of any form such as lamellar, spherical or oblong, irrespective of the crystallographic form (for example cubic, hexagonal, orthorhombic, rhombohedric or tetragonal). In a preferred embodiment, the powders are not spherical.

The number-average size of the powder may range from 0.001 to 50 μm, better still from 0.002 to 40 μm and even more preferentially from 0.003 to 35 μm.

This number-average size corresponds to the size measured from the statistical distribution of the particle sizes for half of the total number of the particles. This size is referred to as the D50.

In addition, the number-average size of these particles may be measured in the form of a mean value via an observation method with a light microscope, an electronic microscope, or a particle size analyser using laser scattering.

In the case where the particles are not in spherical form, their number-average size may be determined in the form of a mean of the longest or shortest diameter or of the thickness.

The composition may preferably comprise one or more powders comprising one or more water-insoluble mineral compounds chosen from metal carbonates, oxides and sulfates and silicates containing magnesium. Preferably, the water-insoluble mineral compound(s) are chosen from calcium carbonate, magnesium carbonate, alumina, barium sulfate and/or magnesium oxide, and better still calcium carbonate.

According to one embodiment, the composition may comprise at least one sebum-absorbing powder with a sebum uptake of greater than or equal to 35 ml/100 g.

For the purposes of the present invention, the term "sebum-absorbing powder" means a powder that is capable of absorbing and/or adsorbing sebum, which has a sebum uptake of greater than or equal to 35 ml/100 g.

The sebum uptake corresponds to the amount of sebum absorbed and/or adsorbed by the powder. It is expressed in ml of sebum per 100 g of powder and is measured using the method for determining the oil uptake of a powder described in standard NF T 30-022.

The oil uptake of a powder corresponds to the amount of sebum absorbed onto the available surface of the powder by measuring the "wet point" as indicated below.

The measuring method is as follows: an amount m (in grams) of between 0.5 and 5 grams of powder is placed on a glass plate, the amount depending on the density of the powder, followed by dropwise addition of artificial sebum having the following composition:

| | |
|---|---|
| triolein | 29% by weight |
| oleic acid | 28.5% by weight |
| oleyl oleate | 18.5% by weight |
| squalene | 14% by weight |
| cholesterol | 7% by weight |
| cholesteryl palmitate | 3% by weight |

After addition of 4 to 5 drops of artificial sebum, the artificial sebum is incorporated into the powder using a spatula, and the addition of the artificial sebum is continued until conglomerates of artificial sebum and of powder form. From this point, the artificial sebum is added at a rate of one drop at a time and the mixture is subsequently triturated with the spatula.

The addition of artificial sebum is stopped when a firm, smooth paste is obtained. This paste must be able to be spread over the glass plate without cracks or the formation of lumps. The volume Vs, in ml, of artificial sebum used is then noted.

The sebum uptake corresponds to the ratio Vs/m.

The sebum-absorbing powder(s) used in the aerosol device of the invention have a sebum uptake preferably ranging from 35 to 1000 ml/100 g and better still from 35 to 800 ml/100 g.

Advantageously, the sebum-absorbing particle may have a BET specific surface area of greater than or equal to 150 $m^2/g$, preferably greater than or equal to 300 $m^2/g$, better still greater than 500 $m^2/g$ and preferentially greater than 600 $m^2/g$, and especially less than 1500 $m^2/g$.

The BET specific surface area is determined according to the BET (Brunauer-Emmett-Teller) method described in the Journal of the American Chemical Society, vol. 60, page 309, February 1938, and corresponding to international standard ISO 5794/1 (appendix D). The BET specific surface area corresponds to the total specific surface area (thus including micropores) of the particle and especially of the powder.

The sebum-absorbing powder may be a mineral powder or an organic powder.

More specifically, the sebum-absorbing powder may be chosen from:
starches,
calcium silicates,
perlites,
zeolites,
polylactic acids,
silicas,
polyamide (Nylon®) powders,
powders of acrylic polymers, especially of polymethyl methacrylate, of poly(methyl methacrylate/ethylene glycol di methacrylate), of poly(allyl methacrylate/ethylene glycol dimethacrylate), or of ethylene glycol dimethacrylate/lauryl methacrylate copolymer;
powders of silicone elastomer, obtained especially by polymerization of organopolysiloxane containing at least two hydrogen atoms each bonded to a silicon atom and of an organopolysiloxane comprising at least two ethylenically unsaturated groups (especially two vinyl groups) in the presence of a platinum catalyst; and
mixtures thereof.

The sebum-absorbing powder may be a powder coated with a hydrophobic treatment agent.

The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "alkyl" mentioned in the compounds cited previously especially denotes an alkyl group containing from 1 to 30 carbon atoms and preferably containing from 5 to 16 carbon atoms.

The starches that may be used in the present invention are, for example, corn starch, potato starch, tapioca starch, rice starch, wheat starch and cassava starch.

The starches may or may not be modified.

A modified starch is a starch that has been modified via processes known to those skilled in the art, for instance esterification, etherification, oxidation, acid hydrolysis, crosslinking or enzymatic conversion.

Non-limiting examples of modified starches include aluminium starch octenylsuccinate, sodium starch octenylsuccinate, calcium starch octenylsuccinate, distarch phosphate, hydroxyethyl starch phosphate, hydroxypropyl starch phosphate, sodium carboxymethyl starch and sodium starch glycolate.

In a particular embodiment, the starch is a starch octenylsuccinate, in particular of aluminium, the starch being corn, wheat or rice starch. Mention may be made especially of the product provided by Akzo Nobel under the name Dry Flo Plus. Mention may also be made of rice starch, such as the product D.S.A.7 provided by the company Agrana Starch.

Preferably, the calcium silicates used as sebum-absorbing powder have a sebum uptake of greater than 200 ml/100 g, better still between 400 ml/100 g and 600 ml/100 g and more preferentially of about 475 ml/100 g.

The specific surface area (BET) preferably ranges from about 150 m²/g to 600 m²/g, better still from 300 m²/g to 600 m²/g and even more preferably from 310 m²/g to 350 m²/g.

The size of the silicate particles is preferably less than 20 micrometres.

These calcium silicates are generally prepared by reaction of reactive silica with an alkaline-earth metal reagent, preferably an alkaline-earth metal oxide or hydroxide, and a source of aluminium such as sodium aluminate or alumina. As the final properties of the silicate depend on the reactivity of the silica, the preferred source of silica is the reaction product of a soluble silicate, such as sodium silicate, and of a mineral acid, such as sulfuric acid. Suitable amorphous synthetic alkaline-earth metal silicates are manufactured by the company J. M. Huber Corporation and are sold under the Hubersorb® names. Methods for preparing these silicas are disclosed in greater detail in patent U.S. Pat. No. 4,557,916. Other suitable silicates are available from J. M. Huber Corporation, such as the sodium aluminosilicate sold under the Zeolexg brand name and the sodium magnesium aluminosilicate sold under the Hydrex® brand name.

Sebum-absorbing powders that may also be used include perlites, which are generally aluminosilicates of volcanic origin and which have the following composition:
70.0%-75.0% by weight of silica $SiO_2$
12.0%-15.0% by weight of aluminium oxide $Al_2O_3$
3.0%-5.0% of sodium oxide $Na_2O$
3.0%-5.0% of potassium oxide $K_2O$
0.5-2% of iron oxide $Fe_2O_3$
0.2-0.7% of magnesium oxide MgO
0.5%-1.5% of calcium oxide CaO
0.05-0.15% of titanium oxide $TiO_2$.

Examples of zeolites that may especially be mentioned include sodium or potassium aluminosilicate compounds such as the product provided by Zeochem under the name XMOL.

The polylactic acids that may be used in the present invention are in particular Accurel EP600 from AkzoNobel or the product provided under the name Lactic Acid Polymer 9105 by Dajac Labs.

Mention may be made, as silica powder, of:

the porous silica microspheres sold under the name Silica Beads SB-700 by the company Miyoshi; Sunsphere® H51, Sunsphere® H33 by the company Asahi Glass;

the polydimethylsiloxane-coated amorphous silica microspheres sold under the name SA Sunsphere® H33 or SA Sunsphere® H53 by the company Asahi Glass.

Mention may be made, as Nylon powder, of the Nylon powder sold under the name Orgasol® 4000 by the company Atochem.

Mention may be made, as acrylic polymer powder, of:

the polymethyl methacrylate powders sold under the name Covabead® LH85 by the company Wackherr;

the polymethyl methacrylate/ethylene glycol dimethacrylate powders sold under the name Dow Corning 5640 Microsponge® Skin Oil Adsorberby the company Dow Corning and the name Ganzpearl® GMP-0820 by the company Ganz Chemical;

the poly(allyl methacrylate/ethylene glycol dimethacrylate) powders sold under the name Poly-Pore® L200 or Poly-Pore® E200 by the company Amcol Health and Beauty Solutions Inc.; these powders have in particular a sebum uptake of greater than or equal to 1 ml/g, better still ranging from 1 ml/g to 20 ml/g;

the ethylene glycol dimethacrylate/lauryl methacrylate copolymer powders sold under the name Polytrap® 6603 from the company Dow Corning.

Mention may be made, as silicone elastomer powder, of the powders sold under the names Trefil® Powder E-505C and Trefil® Powder E-506C by the company Dow Corning.

In a preferred embodiment of the invention, the composition preferably comprises one or more styling powders preferably chosen from mineral powders comprising one or more water-insoluble mineral compounds, more preferentially chosen from metal carbonates, oxides and sulfates, silicates, modified or unmodified silicas, mica and talc, and mixtures thereof, better still from carbonates, in particular calcium carbonate or magnesium carbonate, alumina, barium sulfate and/or magnesium oxide, and better still calcium carbonate.

In this embodiment, the composition may also contain one or more sebum-absorbing powders, preferably chosen from modified or unmodified starch powders.

The powder(s) are present in a total amount of less than 7% by weight, better still in a total amount ranging from 0.1% to 6.9% by weight, better still from 0.5% to 6.5% by weight and even more preferentially from 1% to 6% by weight relative to the total weight of the composition.

In particular, when they are present, the powder(s) comprising one or more water-insoluble mineral compounds chosen from metal carbonates, oxides and sulfates and silicates containing magnesium may be present in an amount of less than 7% by weight, better still in a total amount ranging from 0.1% to 6.9% by weight, better still from 0.5% to 6.5% by weight and even more preferentially from 1% to 6% by weight relative to the total weight of the composition.

The composition may also comprise one or more C2-C4 monoalcohols.

As C2-C4 monoalcohols that may be used in the aerosol device of the invention, mention may be made especially of ethanol or isopropanol, or better still ethanol.

When they are present, the C2-C4 monoalcohol(s) are preferably present in an amount ranging from 1% to 80% by weight, better still from 5% to 70% by weight and even more preferentially from 10% to 65% by weight relative to the total weight of the composition.

The composition according to the invention may contain one or more additional organic solvents such as polyols, for instance glycerol, propylene glycol or polyethylene glycols.

It may also contain water.

Preferably, the composition according to the invention contains less than 5% by weight of water and preferably less than 3% of water relative to the total weight of the composition.

The container of the device according to the invention also comprises one or more propellants.

Examples of propellants that may be used in the aerosol device of the present invention are liquefied gases such as dimethyl ether, 1,1-difluoroethane, or C3-C5 alkanes, for instance propane, isopropane, n-butane, isobutane, pentane or isopentane, or compressed gases such as air, nitrogen or carbon dioxide, and mixtures thereof.

Mention may be made preferentially of C3-C5 alkanes and in particular propane, n-butane and isobutane, and mixtures thereof.

The propellant(s) may be present in the composition or, as a variant, in the container containing the composition, but separate from the composition.

The propellant(s) are preferably present in the composition.

The propellant(s) may be present in a content ranging from 10% to 95% by weight, better still from 15% to 90% by weight and even more preferentially from 20% to 88% by weight relative to the total weight of the composition.

The composition according to the invention may also comprise one or more fixing polymers, preferably chosen from anionic, amphoteric or zwitterionic, and nonionic fixing polymers, better still from anionic or nonionic fixing polymers.

The anionic fixing polymers may be chosen from copolymers of acrylic and methacrylic acid or salts thereof, crotonic acid copolymers, polyacrylamides bearing carboxylate groups, homopolymers or copolymers bearing sulfonic groups, anionic polyurethanes, and anionic-grafted silicone polymers.

The nonionic fixing polymers may be chosen from polyalkyloxazolines; vinyl acetate homopolymers; vinyl acetate copolymers; homopolymers and copolymers of esters; copolymers of acrylonitrile and of a nonionic monomer; styrene homopolymers;

styrene copolymers; polyamides; vinyllactam homopolymers; vinyllactam copolymers; and polyvinyl alcohols.

When the composition comprises one or more fixing polymers, their total content may range from 0.1% to 20% by weight, preferably from 0.5% to 10% by weight and better still from 1% to 8% by weight relative to the total weight of the composition.

The compositions defined in the invention may also comprise one or more additives chosen from silicones, fatty esters, fatty alcohols, anionic, cationic, nonionic, amphoteric or zwitterionic polymers other than the fixing polymers described previously, fragrances, dyes, UV-protective screening agents, acids, bases, nacres and glitter flakes.

These additives may be present in the composition according to the invention in an amount ranging from 0 to 20% by weight relative to the total weight of the composition, when the propellant(s) are present in the composition.

A person skilled in the art will take care to select these optional additives and the amounts thereof so that they do not harm the properties of the compositions of the present invention.

The compositions in accordance with the invention are conditioned in an aerosol device comprising a container, also known as a reservoir.

The container is pressurized and comprises the composition to be dispensed. As already mentioned previously, the container contains both the propellant(s) and the other ingredients of the composition, in a single compartment, or as a variant in two compartments. According to the latter variant, the container may be constituted of an outer aerosol reservoir comprising an inner bag hermetically welded to a valve. The various ingredients of the composition are introduced into the inner bag and a propellant is introduced between the bag and the container at a sufficient pressure to make the composition come out in the form of a spray.

The propellant may be a compressed gas that is preferably used at a pressure of between 1 and 12 bar and better still between 9 and 11 bar.

The container is equipped at its top end with a valve that seals the system. The valves that are suitable for the devices according to the invention are especially valves with an internal restriction orifice of between 0.3 and 3 mm, preferably between 0.5 and 2.5 mm and even more preferentially between 0.6 and 1 mm. As a variant, it is possible for these valves to not comprise an internal restriction orifice. The valves may have a nozzle with at least one orifice, better still two orifices between 0.3 and 1 mm and preferably between 0.4 and 0.8 mm and even more preferentially between 0.5 and 0.7 mm in size. They may also be equipped with an additional gas intake (AGI).

They are in particular "powder" valves sold by the companies Precision, Coster, Seaquist and Lindal.

The device, conditioned with such a valve, ensures the sealing of the system, and also the dispensing of the composition from the container.

The aerosol device according to the invention also comprises a dispensing head comprising a body and an end part, especially a diffuser, which may be connected to the body. The end part comprises at least two outlet orifices configured to allow spraying of the composition about a longitudinal axis Y of the end part in at least two different directions, which may especially be diametrically opposite, the dispensing head comprising at least first and second chambers, through which the composition stream successively passes before it exits via the outlet orifices.

The first and second chambers may be concentric.

At least one aperture between the first and second concentric chambers may be angularly offset relative to at least one of the outlet orifices. This angular offset is to be understood as being an offset about the axis of the concentric chambers or about the axis of the device, for example.

Thus, the composition stream leaving the diffuser has in particular undergone at least two changes of direction of the stream in the diffuser, or even at least three changes of direction. The term "change of direction" should be understood as meaning that the composition stream passes from a first direction to a second direction, the two directions forming between themselves an angle preferably greater than 60°, or even greater than 90°, better still greater than 120°, or even greater than 150°. In one illustrative embodiment, the composition stream undergoes at least one change of direction of greater than 120°, or even greater than 150°, better still of the order of 180°.

When assembled, the body and the end piece may define several outlet orifices about a longitudinal axis Y of the end piece, in particular in at least two different directions, which are in particular diametrically opposite. Alternatively, the dispensing orifices may be formed directly in the diffuser. They may be formed in a curved portion of the diffuser, for example a portion with a hemispherical shape.

The use of the term "end part" does not exclude the possibility that the end piece may comprise an attached element defining the end of the dispensing head.

The concentric chambers may be at least partially annular or, indeed, annular. The dispensing head may in particular comprise a first inner chamber and a second outer chamber. The inner and outer chambers may be separated by a separation skirt. This skirt is able to ensure the leak tightness of the chambers.

This separation skirt may be pierced with at least one aperture, or at least two apertures, allowing the composition stream to pass through. Thus, the composition stream may be separated into at least two distinct streams. The apertures in the separation skirt may be distributed uniformly on the circumference of the separation skirt. For example, they may be diametrically opposite when there are two of them. There may be between 2 and 10 of them.

The second chamber may be surrounded by a peripheral skirt cooperating with the body in such a way as to ensure the closure of the second chamber.

The outlet orifices may be distributed uniformly on the circumference of the peripheral skirt. For example, they are diametrically opposite when there are two of them. There may be between 2 and 10 of them. They may be diametrically opposite in respective pairs.

The dispensing head may be configured to permit spraying of the composition through outlet orifices in at least one direction transverse to a longitudinal axis Y, in particular in at least two different directions, which are in particular diametrically opposite.

The outlet orifices may be coplanar and arranged in an inclined plane relative to the longitudinal axis X. The dispensing head may in particular comprise at least three coplanar outlet orifices, the directions of spraying being in particular arranged at at least 30°, or at least 60°, or at least 90° from each other.

The outlet orifices may be angularly offset relative to the aperture(s) of the separation skirt, each by an angle of between 0 and 180°, better still between 20 and 90°, better still between 30 and 80°, for example of the order of 45°.

The longitudinal axis Y of the diffuser may constitute an axis of symmetry of the diffuser.

The diffuser is preferably assembled with the body via the top of said body. The diffuser may define the upper axial end of the dispensing head.

The end part, in particular the diffuser, may comprise an upper face of generally curved shape with outward convexity.

The dispensing head may have a supply channel for the composition coming from the container. To this end, the body comprises a central channel intended to allow the composition stream to pass from the container to the diffuser.

The body may define a cannula through which said channel extends, this cannula having a longitudinal axis inclined relative to the longitudinal axis X of the container.

The central channel of the body may comprise a vertical portion, which extends in the longitudinal axis X of the device above the container, and an oblique portion, which is inclined by an angle γ relative to the vertical portion. The angle γ may be between 0 and 90°, better still between 5 and 40°, or between 10 and 30°, for example of the order of 15°. The oblique portion of the central channel can receive the diffuser.

The vertical portion of the central channel is intended to receive the stem of the dispensing valve of the container.

The device may be without a nozzle having swirl ducts, which simplifies its production. The dispensing orifices may preferably lead directly to the outside, without an attached nozzle. An attached nozzle is understood as a component having at least one outlet orifice and comprising a plane wall in which the outlet orifice is formed, and also a mounting skirt, which can be mounted on a centre post.

Each jet emerging from the diffuser may be oriented generally along an axis not parallel to a longitudinal axis X of the device, in particular obliquely, for example being inclined relative to the longitudinal axis of the device by an angle greater than 10°, better still greater than 20°, even better still greater than 30°.

The flow emerging from each outlet orifice can be oriented perpendicularly relative to the axis Y of the diffuser, the outlet orifices being coplanar, for example, and having axes oriented perpendicularly relative to the axis Y of the diffuser.

Alternatively, the jet emerging from each outlet orifice can form an angle with the normal to this axis Y, in such a way that all the jets produce a resulting spray of substantially conical shape. This angle may be a non-zero angle, between 5 and 180°, better still between 10 and 90°, or between 20 and 80°, better still between 25 and 70°, for example of the order of 35°.

The device may comprise at least three outlet orifices, better still at least four outlet orifices, which are preferably not aligned. The distance between the farthest outlet orifices can be less than 25 mm, better still less than 20 mm, or less than 15 mm, for example of the order of 12 mm or 10 mm.

The dispensing of the composition can be triggered by tilting the body relative to the container.

A subject of the invention is also the use of the device as described above for spraying a composition through 360°.

Figure 2:
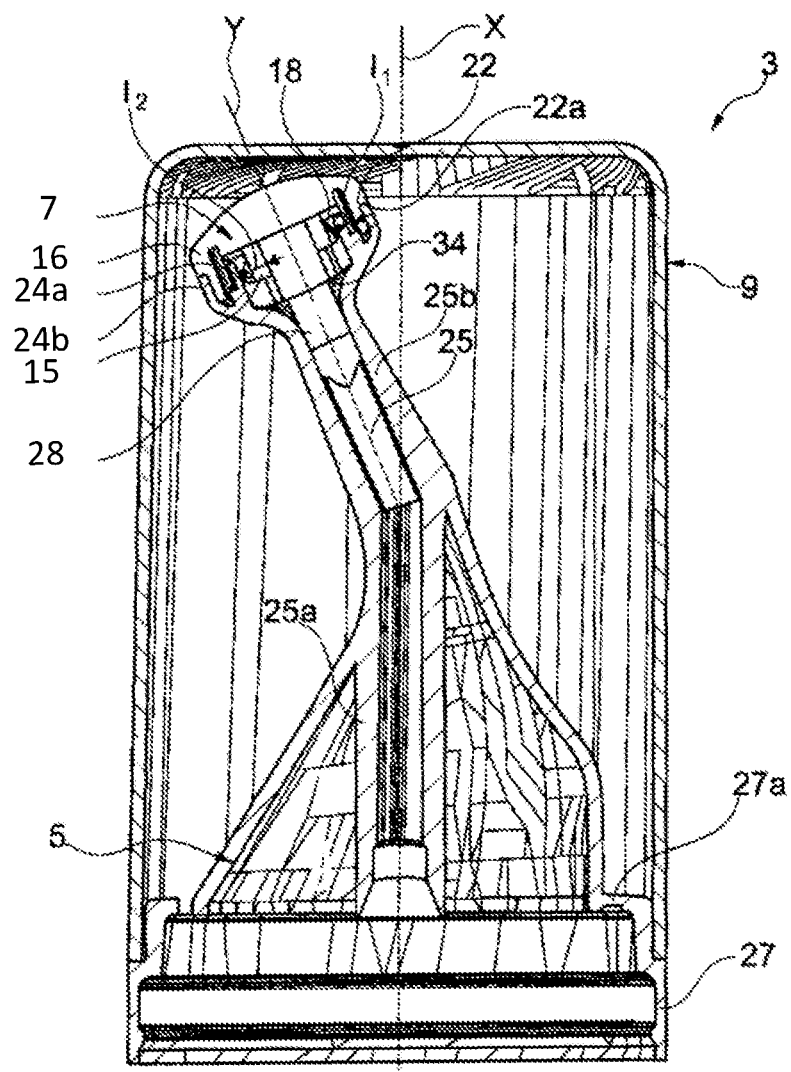
Figure 3:
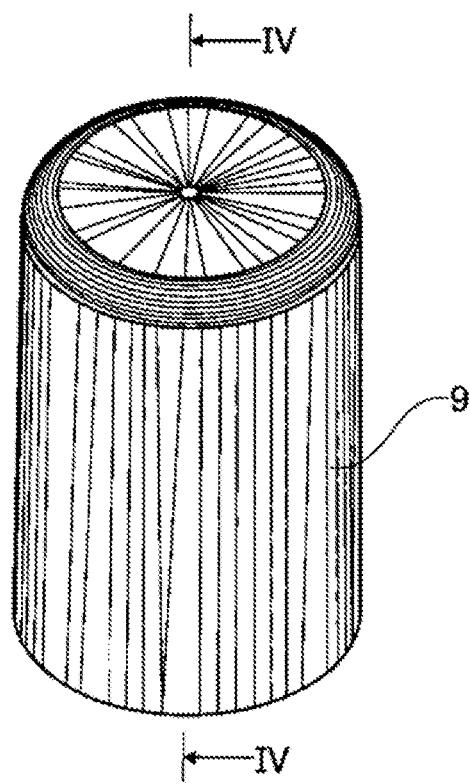
Figure 4:
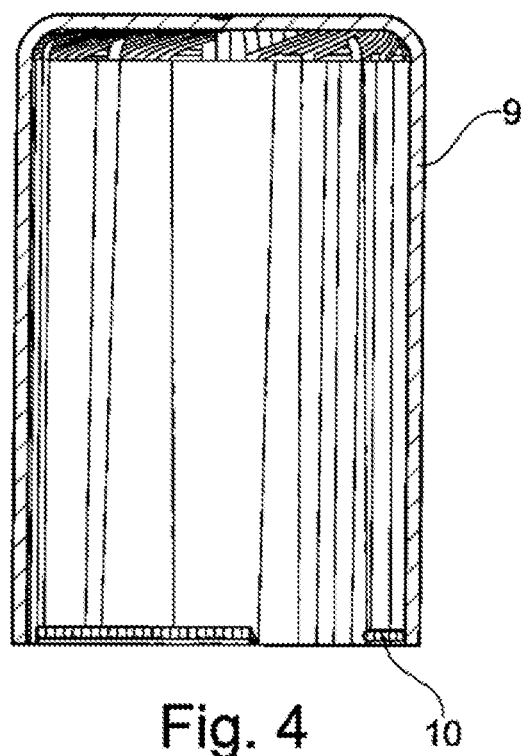
Figure 5:
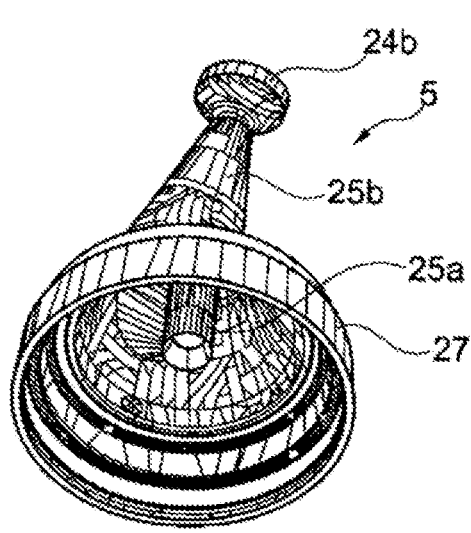
Figure 6:
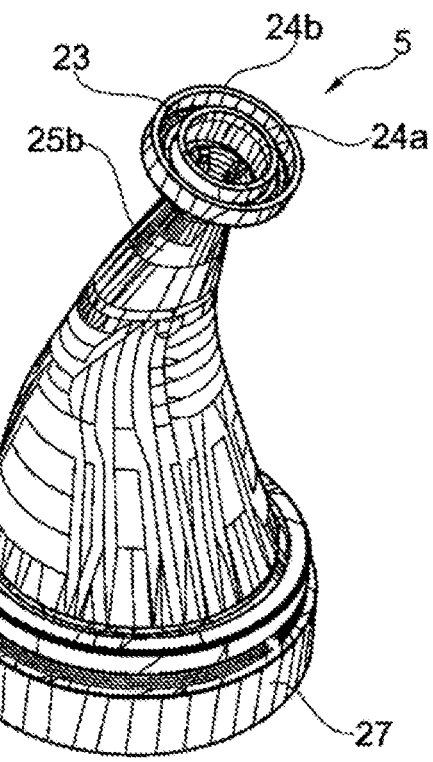
Figure 7:
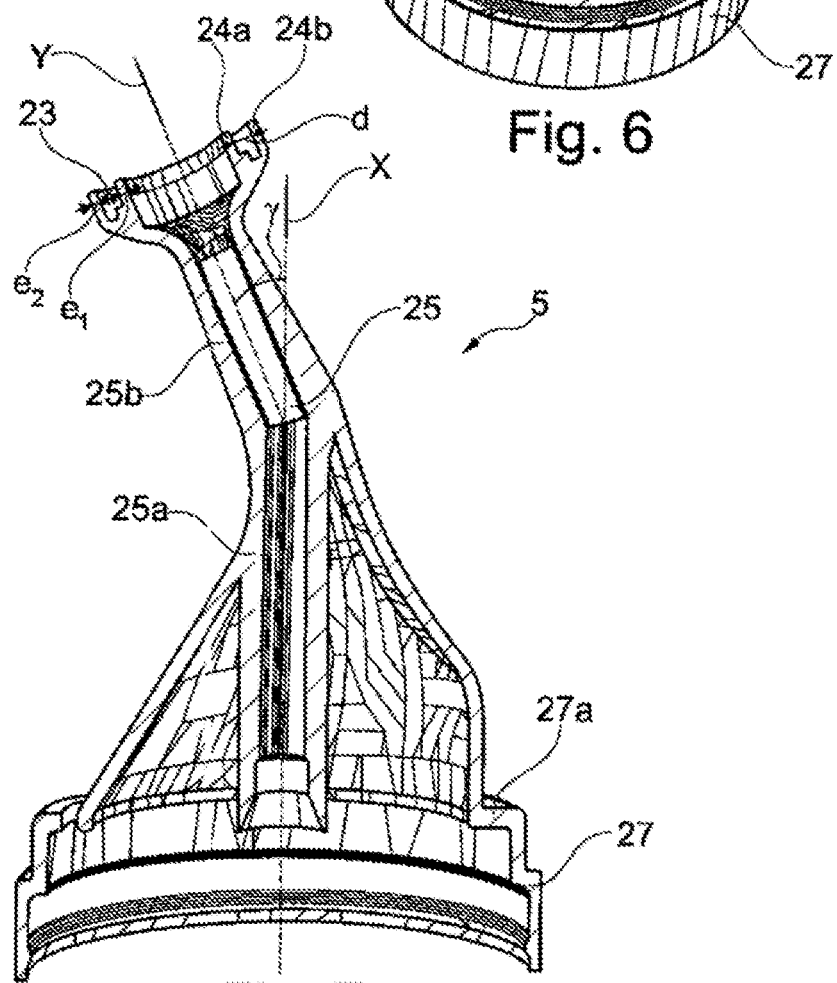
Figure 8:
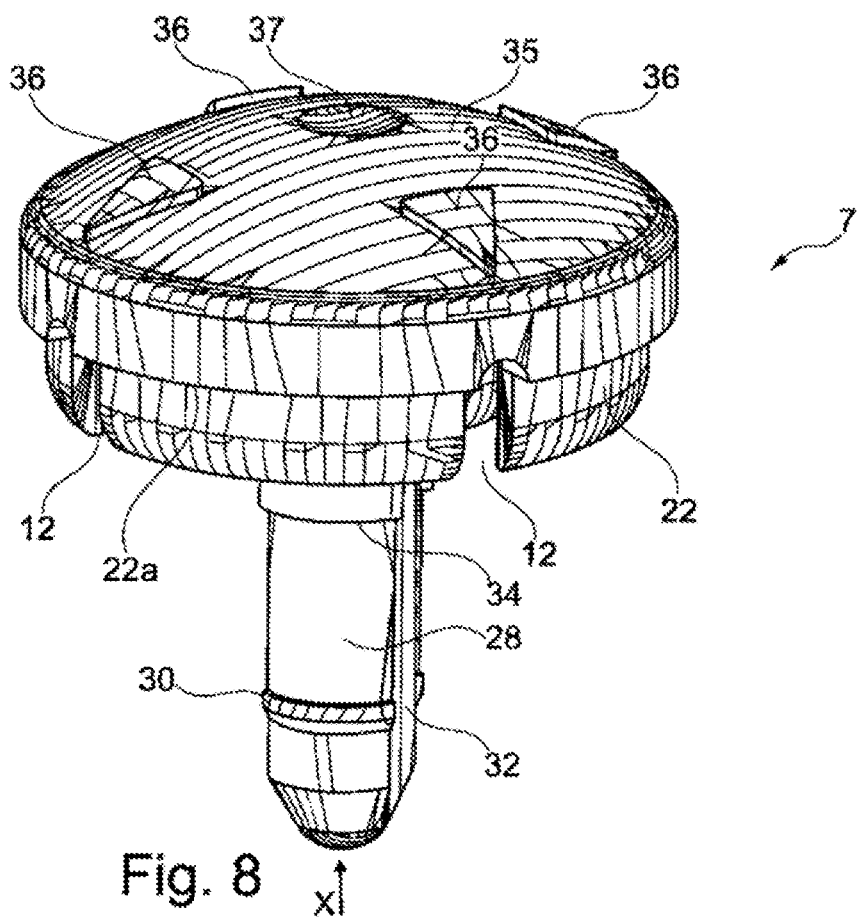
Figure 9:
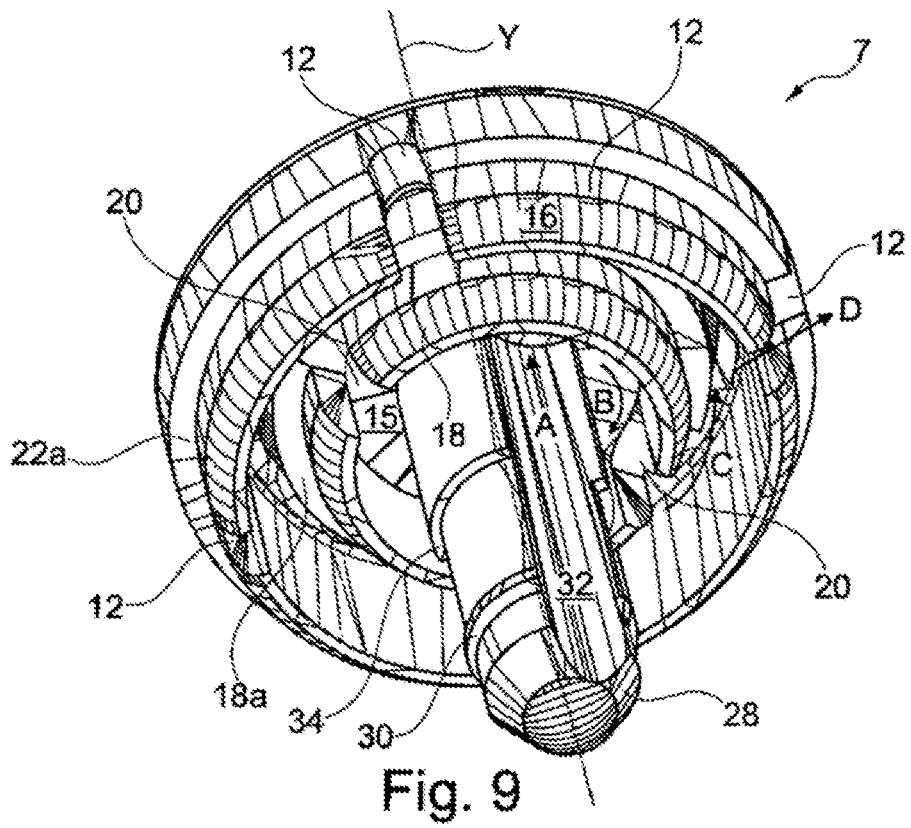
Figure 10:
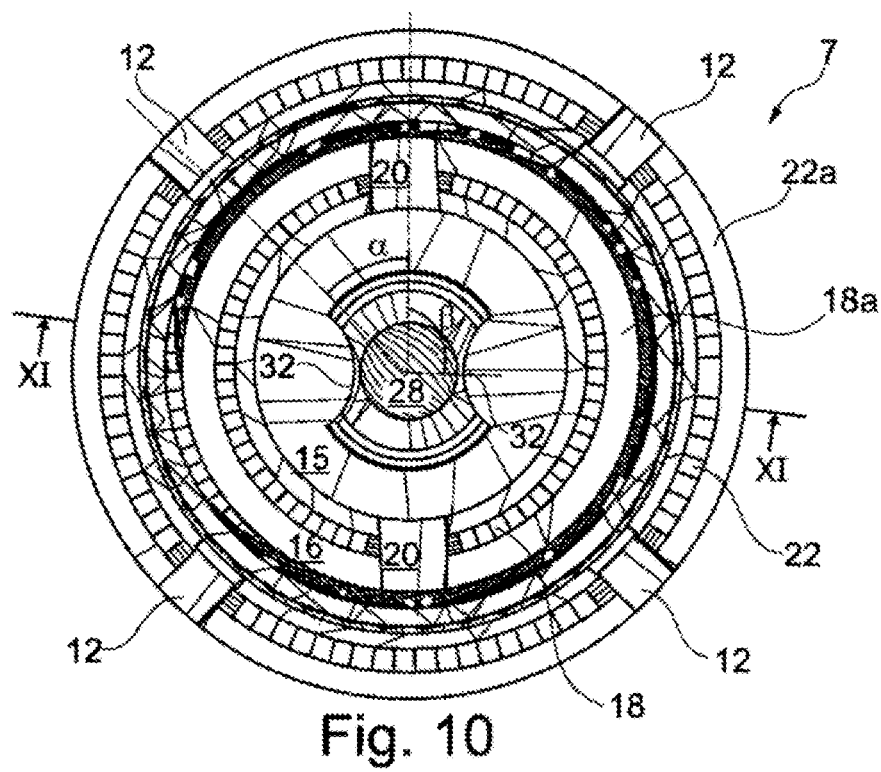
Figure 11:
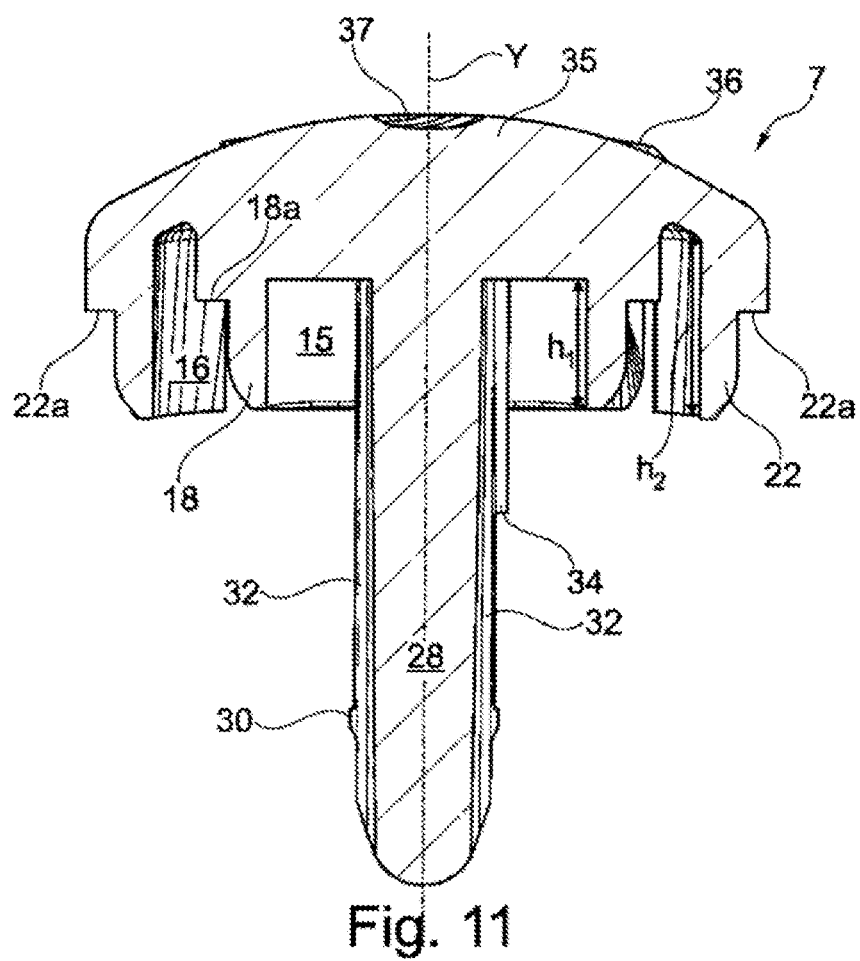
Figure 12:
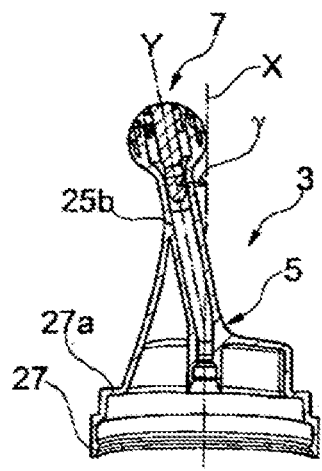
Figure 13:
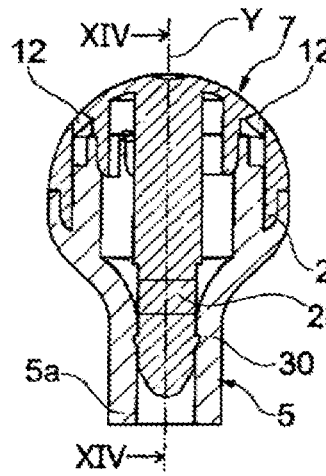
Figure 14:
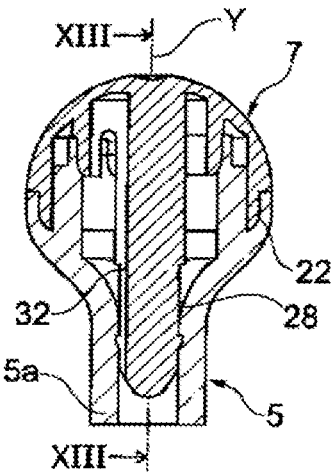
Figure 16:
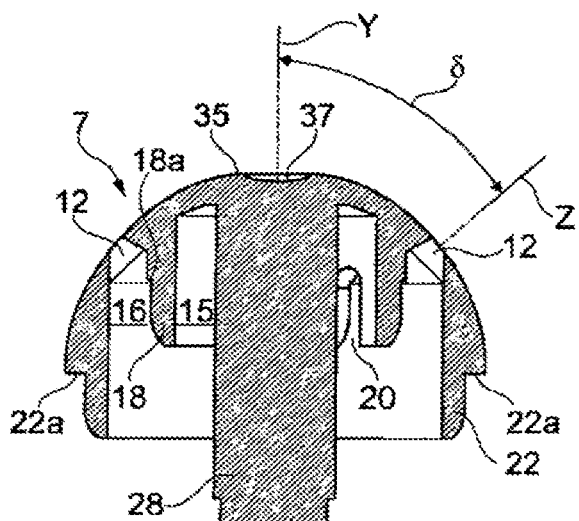
Figure 15:
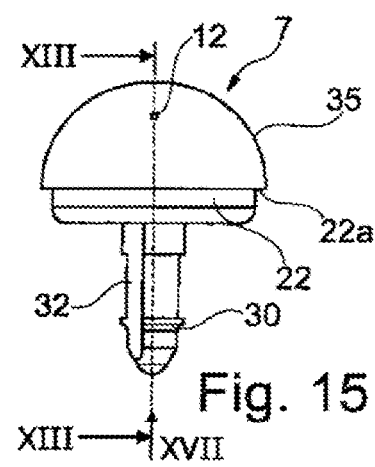
Figure 17:
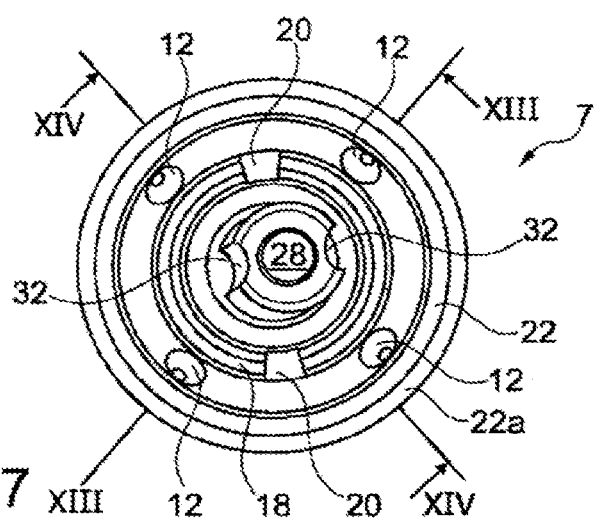
Figure 18:
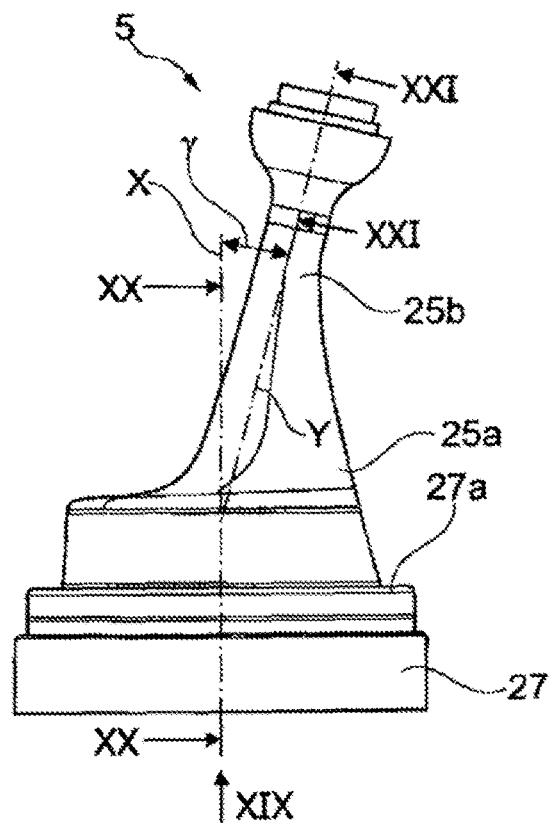
Figure 19:
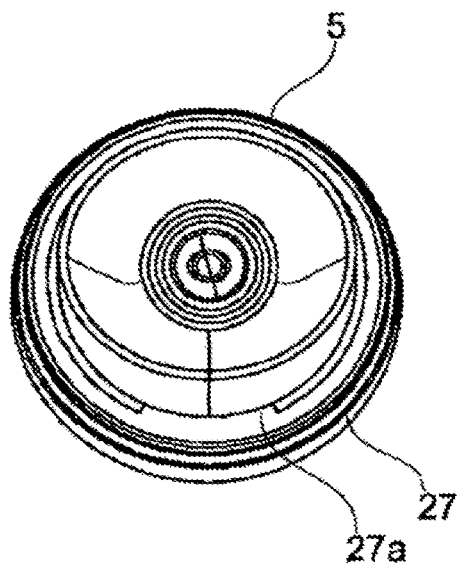
Figure 20:
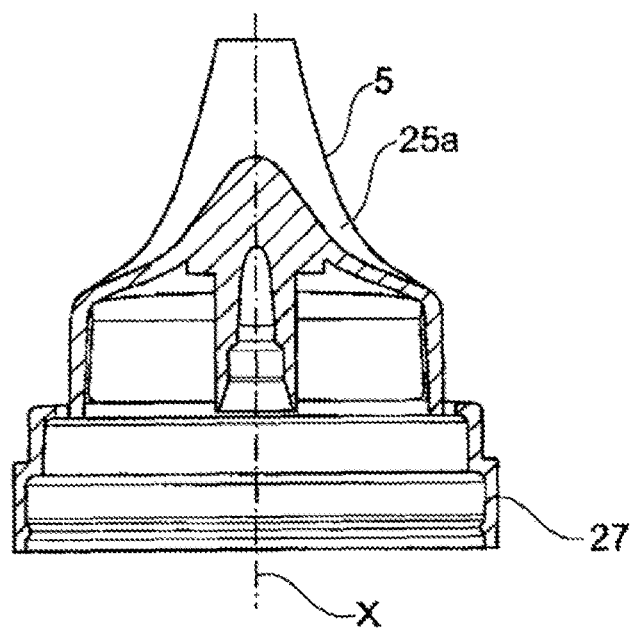
Figure 21:
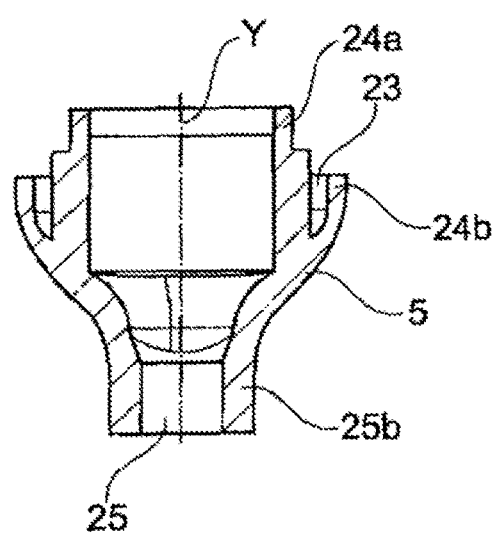

The invention will be understood more clearly on reading the following detailed description of a non-limiting illustrative embodiment thereof and on examining the appended drawing, in which:

FIG. 1 is a side view of a spray device according to the invention,

FIG. 2 is a longitudinal section through the dispensing head of the device in FIG. 1, FIG. 3 is a perspective view of the closure cap of the device in FIGS. 1 and 2, FIG. 4 is a longitudinal section of FIG. 3 along IV-IV, FIGS. 5 and 6 are perspective views of the body of the device in FIGS. 1 and 2, FIG. 7 is a longitudinal section through the body in FIGS. 5 and 6, FIGS. 8 and 9 are schematic and partial perspective views of the diffuser in FIGS. 1 and 2, FIG. 10 is a bottom view along the arrow X in FIGS. 8 and 9, FIG. 11 is a longitudinal section along XI-XI in FIGS. 8 to 10, FIG. 12 is a view, similar to FIG. 7, of an alternative embodiment, FIGS. 13 and 14 are partial longitudinal sections along XIII-XIII and XIV-XIV, respectively, in FIG. 12, FIG. 15 is a perspective view of the diffuser in FIGS. 12 to 14, FIG. 16 is a view, similar to FIG. 13, of the diffuser on its own, FIG. 17 is a view of the diffuser in FIGS. 12 to 16 along the arrow XVII, FIG. 18 is a side view of the body in FIGS. 12 to 17, FIG. 19 is a view thereof along the arrow XIX, FIG. 20 is a cross-sectional view thereof along XX-XX, and FIG. 21 is a cross-sectional view thereof along XXI-XXI.

FIGS. 1 to 11 show a device 1 for spraying a composition, said device 1 comprising a container 2 containing the composition to be sprayed, and a dispensing head 3 which sits on top of the container 2. The initial pressure in the container is, for example, between 1 and 12 bar at 20° C.

The container 2 may comprise a valve holder cup (not shown) crimped onto a body of the container or formed in another way.

The dispensing head 3 comprises a body 5 arranged on the container 2 and cooperating with a diffuser 7. A closure cap 9, visible in FIGS. 3 and 4, is intended to cover the body 5 and the diffuser 7 when the device is not in use. The cap 9 comprises, for example, an annular relief 10 in order to allow it to be held on the container 2 with snap-fit engagement.

The body 5 and the diffuser 7 are configured to allow the composition to be sprayed in at least two different directions, of which there are four in the example described and are distributed uniformly about the axis Y of the diffuser. For this purpose, the diffuser 7 comprises four outlet orifices 12, visible in FIGS. 8 to 10, which will be described in detail below.

During the spraying of the composition, the composition stream coming from the container firstly passes through a central channel 25 of the body 5, which is intended to allow the composition to pass from the container 2 as far as the diffuser 7. This central channel 25 comprises a straight portion 25a, which extends in the longitudinal axis X of the device above the container, and an oblique portion 25b, which extends along the axis Y of the diffuser 7 and which is inclined by an angle γ relative to the straight portion 25a. The angle γ is of the order of 20 to 30°, for example.

The diffuser 7 comprises a central stem 28 allowing it to be fixed to the body 5, in the oblique portion 25b. It is fixed by being inserted by force and with snap-fit engagement. For this purpose, the central stem 28 comprises a fixation relief 30, such as an annular bead, intended to snap-fit behind a corresponding relief of the body 5.

The central stem 28 has a shoulder 34 in order to guarantee leak tightness.

Two longitudinal grooves 32 formed on the central stem 28 allow the composition to pass from the body 5 towards the diffuser 7. They are diametrically opposite each other in the example described. These grooves 32 are oriented along the axis Y of the diffuser. They may have a cross section that is partially circular.

In the diffuser 7, the composition stream passes through a first inner chamber 15 and a second outer chamber 16 concentric to the first.

The diffuser 7 comprises a separation skirt 18 between the first and second chambers 15 and 16. This separation skirt 18 is pierced with two apertures 20 to allow the composition stream to pass through. The latter is thus separated into four distinct streams, of which two opposite streams each emerge from the apertures 20. The latter are uniformly distributed on the circumference of the separation skirt 18, being diametrically opposite each other. Each aperture 20 preferably extends along the entire height h1 of the separation skirt 18, as is illustrated in FIG. 11. The height h1 of the separation skirt 18 is of the order of 2.5 or 4 mm, for example.

The second chamber 16 is surrounded by a peripheral skirt 22 of the diffuser 7, said peripheral skirt 22 cooperating with the body 5 in such a way as to ensure the closure of the second chamber 16. The peripheral skirt 22 comprises the four abovementioned outlet orifices 12 for ensuring the discharge of the composition to the outside. These outlet orifices 12 are distributed uniformly about the axis Y of the diffuser 7. They may each extend along the entire height h2 of the peripheral skirt or along only part thereof. This height h2 may be of the order of 1.9 or 5 mm.

The chambers 15 and 16 preferably have respective widths l1 and l2 of the order of 1.2 mm.

The outlet orifices 12 may comprise a lower portion, in the form of a slit of constant width formed in the bottom of the skirt 22, and an upper portion, which has a semicircular cross section and is formed in the top of the skirt 22, extending away from the shoulder 22a. The composition emerges from the device via the upper portion of the outlet orifices 12, the lower portion being masked and closed by the body 5.

The outlet orifices may each have a cross section of between 0.05 and 5 mm$^2$, better still between 0.1 and 2 mm$^2$, for example of the order of 1 mm$^2$.

The outlet orifices may have any suitable geometric shape. In one embodiment, they may have a circular cross section.

The outlet orifices 12 are offset angularly relative to the apertures 20 of the separation skirt 18. For example, they are each offset by an angle α of the order of 45°, as illustrated in FIG. 10.

The apertures 20 are offset relative to the longitudinal grooves 32. For example, they are offset by an angle β of the order of 90°, as illustrated likewise in FIG. 10.

The body 5 comprises an annular groove 23 intended to receive the peripheral skirt 22 of the diffuser 7. This annular groove 23 is delimited by two concentric ribs 24a and 24b which are configured to engage on each side of the peripheral skirt 22. The two ribs 24a and 24b are continuous. They can bear against shoulders 22a and 18a, which are present on the separation skirt 18 and the peripheral skirt 22 respectively, when the body and the diffuser are assembled. They preferably have respective thicknesses e1 and e2 of the order of 0.7 mm. They form between them a distance d of the order of 1.25 mm. The rib 24b closes the lower portion of the outlet orifices 12.

The annular groove 23 and the ribs 24a and 24b are arranged at an end of the body opposite a mounting skirt 27 for mounting the body 5 on the container 2. The rest of the body, in particular the central channel 25 of the body, is connected to the mounting skirt 27 by a hinge 27a. The mounting skirt is preferably fixed with snap-fit engagement on the container, but it may also be fixed to the latter in another way.

The diffuser 7 has an upper face 35 with a generally curved shape, of which the radius of curvature is, for example, of the order of 6 mm.

The upper face 35 of the diffuser 7 has markers in the form of reliefs 36 with the general shape of a triangle, of which the point is oriented towards the edge of the upper face 35 and towards the peripheral skirt 22 in the alignment of the outlet orifices 12. The upper end 35 of the diffuser 7 likewise has a central depression 37, which has a circular contour and accommodates the injection sprue.

The composition stream undergoes at least two changes of direction in the diffuser 7. As illustrated in FIG. 9, the composition stream thus passes from a first direction A in the grooves 32 to a second direction B in the first chamber 15, the two directions A and B forming between them an angle of 90°. The composition stream then passes from the direction B to a direction C in the second chamber 16, with a change of direction of the order of 180°, then adopts a direction D corresponding to the emergence of the composition through an outlet orifice 12.

An alternative embodiment will now be described with reference to FIGS. 12 to 21. In this example, the outlet orifices 12 are formed in the diffuser 7 directly. They are formed in a curved portion of the diffuser 7, of hemispherical shape, having a radius of curvature of the order of approximately 6 mm.

The orifices 12 are each oriented outwards on an axis Z, which forms an angle δ with the axis Y of the diffuser. The angle δ is less than 90°, such that the resulting spray is of conical shape, with the composition being distributed all around the axis Y. The angle δ may be between 10 and 85°, better still between 20 and 80°, for example between 30 and 75°, or between 40 and 70°. It can be of the order of 60°, for example.

The dispensing head in FIGS. 12 to 21 also differs from that of FIGS. 1 to 11 in terms of the shape of the body 5. In this illustrative embodiment, the latter comprises a cannula 25b through which said channel 25 extends, this cannula having a longitudinal axis Y inclined relative to the longitudinal axis X of the container.

In addition, the mounting skirt 27 for mounting the body 5 on the container 2 is connected to the rest of the body by a hinge 27a situated, relative to the longitudinal axis X, on the same side as the inclination of the axis Y, in such a way that the longitudinal axis Y of the cannula of a movable part of the body 5 is substantially parallel to the longitudinal axis X of the container during the dispensing of the composition.

The invention is not limited to the examples that have just been described.

For example, the valve of the container can be triggered by being pushed down and not by tilting.

The number of outlet orifices may be modified, as may their orientation.

The axes of the outlet orifices, along which axes the sprays are emitted, may or may not be coplanar, or they may or may not be contained in the same cone of axis Y.

The example that follows serves to illustrate the invention.

EXAMPLES

In the examples that follow, all the amounts are indicated as weight percentage of product as active material relative to the total weight of the composition.

The following compositions were prepared from the compounds indicated in the table below.

|  | 1 | 2 | 3 |
|---|---|---|---|
| Aluminium starch octenylsuccinate[1] | 1.72% | 1.72% | — |
| Calcium carbonate (D50 = 35 μm)[2] | 1.00% | 5.00% | 3.00% |
| Hectorite modified with distearyldimethylammonium chloride[3] | 0.50% | 0.25% | — |
| Polyvinylcaprolactam | 2% | — | — |
| VA/crotonates/vinyl neodecanoate copolymer[4] | — | — | 1.00% |
| Octylacrylamide/acrylates/butylaminoethyl methacrylate copolymer[5] | — | — | 4.5% |
| Aminomethylpropanol | — | — | 0.85% |
| Ethanol | qs 100% | qs 100% | Qs 100% |
| Dimethicone | 0.48% | — | — |
| Dimethiconol | 0.06% | — | — |
| Water | 0.29% | 0.28% | — |
| Butane | 60% | 70% | — |
| Dimethyl ether | — | — | 40% |

[1]Sold under the trade name Dry Flo Plus by National Starch (86% AM)
[2]Sold under the trade name Omyacare S60 by Omya
[3]Sold under the trade name Bentone 38 by Elementis
[4]Sold under the trade name Resyn 28-2930 by Akzo Nobel
[5]Sold under the trade name Amphomer by AkzoNobel Compositions 1 to 3 were packaged in a device D1 according to the invention as shown in FIGS. 12 to 21. It comprises the following characteristics:
 a 150 ml container containing the composition;
 a valve equipped with a nozzle with an orifice 0.5 mm in size and an internal restriction orifice for the valve body 0.8 mm in size, with an additional gas intake 0.40 mm in size,
 a dispensing head comprising a cannula which ends with a dome-shaped wall equipped with four outlet orifices of coplanar axes, perpendicular to the longitudinal axis (Y) of the cannula, and uniformly distributed about the axis Y, the four orifices being diametrically opposite in respective pairs. The outlet orifices have a cross section of 1 mm². The dispensing head comprises two concentric chambers communicating via two apertures offset by an angle α of the order of 45° relative to the outlet orifices.

The compositions were sprayed on a malleable head of shoulder-length hair. The application is performed with the head hanging down, at the roots, followed by working with the fingers to spread the composition throughout the roots.

Imparting a good level of volume is achieved, while at the same time maintaining supple hair and a natural look.

An aerosol device D2 was moreover used to package composition 1 above. It comprises the following characteristics:
 a valve equipped with a nozzle with an orifice 0.64 mm in size and an internal restriction orifice 0.64 mm in size, with an additional gas intake 0.64 mm in size,
 a dispensing head sold by the company Lindal under the name Tribuse and described in patent application EP 2 991 612, equipped with three orifices whose outlet axes are in the same direction, with a direct outlet 0.5 mm in diameter.

Composition 1 is applied via these two aerosol devices in comparison on six volunteers. In both cases, the same amount of composition was sprayed. The application is performed at the root, by six sprays per half-head, followed by working with the fingers. Evaluation is performed after drying the product.

The performance in terms of ease of shaping was evaluated by experts on six volunteers, on a scale ranging from 0 (poor) to 5 (very good).

The grades and averages obtained are given below:

|  | Composition 1 with D1 | Composition 1 with D2 |
|---|---|---|
| Expert 1 | 5 | 2.5 |
| Expert 2 | 5 | 3.5 |
| Expert 3 | 5 | 3.5 |
| Expert 4 | 5 | 3.5 |
| Expert 5 | 5 | 3.5 |
| Expert 6 | 5 | 3.5 |
| Ave. | 5 | 3.3 |
| Standard deviation | 0.0 | 0.4 |

Device D1 according to the invention made it possible to improve the ease of shaping.

The invention claimed is:

1. An aerosol device comprising:
 a container containing a cosmetic composition that comprises less than 7% by weight of a powder, relative to the total weight of the composition; and
 a dispensing head comprising:
  a body disposed on the container;
  a diffuser disposed on the body and comprising:
   a peripheral skirt comprising outlet orifices configured to spray the cosmetic composition in different directions with respect to a longitudinal axis of the diffuser;
   a separation skirt disposed within the peripheral skirt and comprising apertures;
   a central stem disposed within the separation skirt and comprising at least one longitudinal passage;
   a first chamber formed between the central stem and the separation skirt; and
   a second chamber formed between the separation skirt and the peripheral skirt and concentrically surrounding the first chamber,
  wherein:
   the diffuser is configured such that during dispensing, a portion of the cosmetic composition flows through the longitudinal passage in a first flow direction, flows through the first chamber in a flow second direction, flows through the second chamber in a third flow direction, and then flows through one of the outlet orifices in a fourth flow direction, with the first, second, third, and fourth flow directions being different from one another; and the second and third flow directions are coaxial with respect to the longitudinal axis of the diffuser.

2. The aerosol device of claim 1, wherein:
a difference between the first flow direction and the second flow direction is about 90°; and
the second flow direction and the third flow direction are opposite coaxial directions.

3. The aerosol device of claim 1, wherein the powder comprises a water-insoluble mineral compound chosen from metal carbonates, metal oxides, metal sulfates, magnesium silicates, or any combination thereof.

4. The aerosol device of claim 3, wherein the water-insoluble mineral compound chosen from calcium carbonate, magnesium carbonate, alumina, barium sulfate and/or magnesium oxide, or any combination thereof.

5. The aerosol device of claim 1, wherein the powder comprises a sebum-absorbing powder having a sebum uptake of greater than or equal to 35 ml/100 g.

6. The aerosol device of claim 5, wherein the sebum-absorbing powder is chosen from starches, calcium silicates, perlites, zeolites, polylactic acids, silicas, polyamide powders, acrylic polymer powders, silicone elastomer powders, or any combination thereof.

7. The aerosol device of claim 5, wherein the sebum-absorbing powder comprises a modified starch chosen from aluminum starch octenylsuccinates, perlite, polylactic acids, zeolites, or any combination thereof.

8. The aerosol device of claim 1, wherein relative to the total weight of the cosmetic composition, the powder is present in a total amount ranging from 0.1% to 6.9% by weight.

9. The aerosol device of claim 1, wherein relative to the total weight of the cosmetic composition, the cosmetic composition comprises water in an amount of less than 5% by weight.

10. The aerosol device of claim 1, wherein the cosmetic composition comprises a propellant chosen from air, nitrogen, carbon dioxide, dimethyl ether, n-butane, propane, isobutene, isopentane, 1,1-difluoroethane, or any combination thereof.

11. The aerosol device of claim 10, wherein relative to the total weight of the composition, the cosmetic composition comprises the propellant in an amount ranging from 10% to 95% by weight.

12. The aerosol device of claim 1, wherein the cosmetic composition comprises a fixing polymer chosen from anionic fixing polymers, amphoteric fixing polymers, non-ionic fixing polymers, or any combination thereof.

13. The aerosol device of claim 1, wherein axes of the outlet orifices are coplanar and extend perpendicular to the longitudinal axis of the diffuser.

14. The aerosol device of claim 1, wherein the diffuser comprises a dome-shaped wall comprising the outlet orifices.

15. The aerosol device of claim 1, wherein the body defines a cannula that extends along the longitudinal axis and is inclined relative to a longitudinal axis of the container.

16. The aerosol device of claim 1, wherein with respect to the longitudinal axis, the longitudinal passage is radially offset from the apertures, and the apertures are radially offset from the outlet orifices.

17. A method of shaping hair, the method comprising:
spraying the hair with an effective amount of a cosmetic composition;
wherein the cosmetic composition comprises a powder in an amount of less than 7% by weight, relative to the total weight of the composition;
wherein the cosmetic composition is sprayed from a dispensing head comprising:
a body disposed on the container;
a diffuser disposed on the body and comprising:
a peripheral skirt comprising outlet orifices configured to spray the cosmetic composition in different directions with respect to a longitudinal axis of the diffuser;
a separation skirt disposed within the peripheral skirt and comprising apertures;
a central stem disposed within the separation skirt and comprising at least one longitudinal passage;
a first chamber formed between the central stem and the separation skirt; and
a second chamber formed between the separation skirt and the peripheral skirt and surrounding the first chamber,
wherein:
the diffuser is configured such that during dispensing, a portion of the cosmetic composition flows through the longitudinal passage in a first flow direction, flows through the first chamber in a flow second direction, flows through the second chamber in a third flow direction, and then flows through one of the outlet orifices in a fourth flow direction, with the first, second, third, and fourth flow directions being different from one another; and
the second and third flow directions are coaxial with respect to the longitudinal axis of the diffuser.

18. The method of claim 17, wherein the method further comprises rinsing the hair after spraying the cosmetic composition on the hair.

19. The method of claim 17, wherein the method further comprises:
wetting the hair before the composition is sprayed onto the hair; and
drying the hair after the composition is sprayed onto the hair.

20. The method of claim 17, wherein:
with respect to the longitudinal axis, the longitudinal passage is radially offset from the apertures, and the apertures are radially offset from the outlet orifices;
a difference between the first flow direction and the second flow direction is about 90°; and
the second flow direction and the third flow direction are opposite coaxial directions.

* * * * *